US 7,672,807 B2

United States Patent
Wen (10) Patent No.: US 7,672,807 B2
(45) Date of Patent: Mar. 2, 2010

(54) ULTRASONIC COLOR IMAGING CHARACTERIZING ULTRA-FINE STRUCTURES AND CONTINUOUSLY DISTRIBUTED PHYSICAL CONDITIONS

(76) Inventor: Jing Jiang Wen, 128 Powder Mill Rd., Sudbury, MA (US) 01776

( * ) Notice: Subject to any disclaimer, the term of this patent is extended or adjusted under 35 U.S.C. 154(b) by 180 days.

(21) Appl. No.: 11/504,231

(22) Filed: Aug. 15, 2006

(65) Prior Publication Data
US 2007/0047831 A1 Mar. 1, 2007

Related U.S. Application Data

(60) Provisional application No. 60/707,940, filed on Aug. 15, 2005.

(51) Int. Cl.
  G01C 19/00 (2006.01)
  G01B 5/14 (2006.01)
  G01B 7/14 (2006.01)
  G01B 11/14 (2006.01)
(52) U.S. Cl. ...................................... 702/150; 702/159
(58) Field of Classification Search ................. 702/150, 702/159, 171, 48, 54; 600/437, 438, 447; 382/162, 164, 167; 345/157, 589, 634, 640
See application file for complete search history.

(56) References Cited

U.S. PATENT DOCUMENTS

| 5,860,928 A | 1/1999 | Wong et al. |
| 6,571,018 B1 | 5/2003 | Kim |
| 6,579,240 B2 | 6/2003 | Bjaerum et al. |
| 2006/0184028 A1* | 8/2006 | Wen ........................... 600/441 |

FOREIGN PATENT DOCUMENTS

WO  2005/023117  * 3/2005

* cited by examiner

Primary Examiner—Michael P Nghiem (57) ABSTRACT

This invention discloses methods and apparatus for ultrasonic color imaging that characterizes ultra-fine structures and distributional physical conditions within the target under inspection. The disclosed complementarily incorporates information arising from a plurality of repeated sound trips forced by repeated reflections of exterior and interior interfaces of target, and expresses the information into an image segment representing the main path that ultrasonic signals traveled within the target. The image produced is substantially more discriminative, descriptive, and position-sensitive to both acoustic interfaces and distributional acoustic characteristics of the target. The invention is especially useful for thin sheet targets most vulnerable to both non-continuous and continuous interior defects. The continuous interior conditions and effects of ultra-thin layered structures, that traditional ultrasonic inspection has been unable to express, are effectively expressed by linking their effects of deforming the waveform of passing ultrasonic signals to color image details.

10 Claims, 4 Drawing Sheets

Flow chart of prior art brightness imaging vs. present invention

Fig. 1 Signal trace obtained on a 5 mm thickness calibrator

Fig. 2 Signal trace obtained on a 1 mm thickness calibrator

Fig. 3 Acoustic impulse response derived from the signal trace in Fig. 2.

Fig. 4: Color composition of an image segment from a cross-sectional profile image. Due to the fact that the patent rules on drawing don't allow color images that can't be reliably reproduced by copy machines, the RGB color compositions are provided instead of actually coloring the image.

Fig. 5: Flow chart of prior art brightness imaging vs. present invention

Fig. 6: Data retrieval, processing, storage and display

ULTRASONIC COLOR IMAGING CHARACTERIZING ULTRA-FINE STRUCTURES AND CONTINUOUSLY DISTRIBUTED PHYSICAL CONDITIONS

CROSS-REFERENCE TO RELATED APPLICATIONS

This application claims the benefit of U.S. provisional application "Ultrasonic Sectional Profiling Using Multi-Reflection Information in Multi-Parameter Color Image Presentation", Ser. No. 60/707,940, filed on Aug. 15, 2005 by the present inventor.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISK

None.

VOCABULARY AND DEFINITIONS

Trace, signal trace, amplitude trace, amplitude response: All these phrases are used to refer to same thing—varying signal amplitude as a function of time. It is also known as "A-Scan" (meaning Amplitude-Scan) in ultrasonic NDT community. Usually can be directly and reliably obtained, a signal trace provides the most first-hand information resource for almost all ultrasonic inspections, including thickness gauging, flaw detection, and imaging.

Main path associated with a trace: In typical situations of ultrasonic inspection, after a detecting ultrasound signal is launched into a target being inspected, multiple ultrasound echoes are generated by multiple reflections between the front wall and back wall of the target. The common path of all these echoes is a straight line perpendicular to the front wall. It often coincides with the transducer axis if the front wall surface of target is flat and in good contact with the transducer surface. That common echo path is the main path associated with the trace. Some portions of ultrasound signals do depart from the main path in propagation because of scattering, diffraction, incident angle of reflections, etc., that why a phrase "main path" seems necessary. A main path is actually associated with a transducer position at which the trace is retrieved.

Imaging parameters: an equivalence of "procedure parameter", "intermediate parameter", or "operation parameter" widely found in literatures on hardware and software of digital equipments. Since the "procedure" and "operation" in this document focus on image or imaging, "imaging parameter" is used wherever "procedure parameter", "intermediate parameter", or "operation parameter" can be used. An imaging parameter can be a physics parameter, a mathematics parameter, a signal parameter and other parameter.

Color parameter: typical color images use three quantities to uniquely specify the display color of each and every image point. For example, in most widely used RGB (Red-Green-Blue) color scheme, three dimensionless numerical values are used to specify the amount of Red, Green and Blue respectively. These dimensionless numerical values are referred to as color parameters. Besides RGB and RYB (Red, Yellow, Blue), RYGB (Red, Yellow, Green, Blue), some six-base-color color schemes also have been reported and actually employed in color imaging equipments or medium platforms.

BACKGROUND OF THE INVENTION (1) Field of the Invention

The present invention relates to the field of non-destructive ultrasonic medical and industrial inspections. In particular it relates to ultrasonic color imaging for medical and material inspection and characterization.

(2) Description of Related Art

Taking advantage of the fact that ultrasound can travel through article bodies unreachable by human vision, ultrasonic inspection has been widely employed in industrial material inspection and medical diagnosis for a long time. When a traveling ultrasound signal encounters an acoustical interface dividing two materials of different acoustic impedances, a portion of ultrasound energy enters into the forward material, while the remaining part of signal energy is bounced back to the backward material, generates a detectable ultrasound echo revealing the existence of the interface. Acoustical interfaces capable of generating ultrasound echoes include the exterior surfaces enclosing the target body, as well as the interior discontinuities such as layered structures, voids, cracks, impurities and any abrupt changes in acoustic impedance.

The most popular ultrasonic inspection products can be classified into three major categories: Ultrasonic thickness gauges, Ultrasonic flaw detectors, and Ultrasonic imaging systems.

Ultrasonic thickness gauges measure the time span between two echoes reflected by two interfaces of interest, typically the front and back walls of the target. The thickness, i.e. the distance between the two walls, is readily calculated through the measured time span and the sound speed of the target material. Numerical thickness readings are then displayed on a screen or stored in a data file.

Ultrasonic flaw detectors display a selected portion of received signal trace carrying information about the target interior. Interior discontinuities on the traveling path of incident ultrasound reflect the passing signal, causing extra echoes to appear in the received signal trace. Advanced flaw detectors provide auxiliary tools such as programmable gates, thresholds, cursors, etc, to help locating echoes of predetermined amplitudes within predetermined ranges.

Ultrasonic imaging systems rely on moving an ultrasound beam across the target surface to produce an image of the target interior. The scan of sound beam can be realized either by mechanically moving the probe, or by electronically moving the sound beam formed by a phased transducer array. The produced images are either cross-sectional profiles perpendicular to the scan surface, or a reflecting interface underneath and roughly parallel to the scan surface. The brightness of each image point is determined by the intensity of the echo signal attributable to the corresponding field point within the target.

In all three categories of ultrasonic inspections described above, it is the geometries of the exterior and interior discontinuities that are actually being studied. As a matter of fact, for every field point on an interface, there could be multiple echoes providing information, and each echo supplying a series of numerical data representing signal amplitude as a function of time; In sharp contrast, for all image points between the interfaces (not on the interfaces), there are no data representing/describing them. That is why traditional ultrasonic inspection only inspects interfaces (or discontinuities) within the target.

Many critical physical conditions without distinct geometric boundaries, such as variations in elasticity, density, hardness, stiffness, strength, compositional distribution, metallographic properties, etc. may develop due to diseases, medical treatments, machine processing, material fatigue, uneven strain stresses, temperature gradations, physical strikes, prolonged exposure to physical or chemical effects, etc., are potentially harmful but not in the scope of ultrasonic inspections. It would be highly desirable to detect such conditions before they develop into fatal discontinuities like cracks. Unfortunately, traditional ultrasonic inspections only deal with discontinuities, not continuously distributed conditions.

In traditional ultrasonic imaging, only one parameter, typically the peak amplitude of the first echo, is used as the across board imaging parameter. Field points producing echoes of same peak amplitude are represented with same brightness, therefore seem identical to image viewers. It can not be farther from the truth. In fact, echoes with equal peak amplitudes can be quite different in their waveforms. The waveform difference can reveal critical difference not only about two field points, but also about the paths that the sound traveled to reach each field points. Unfortunately, such invaluable information has been left unused in conventional ultrasonic imaging for decades.

A major improvement was disclosed by the present inventor in patent application "Methods and Apparatus for Ultrasonic Color Imaging", Application Number 2004100745612 filed with China patent office on Sep. 8, 2004, PCT Application Number PCT/CN2004/001030 on Sep. 8, 2004, and application Ser. No. 11/369,603 filed with USPTO on Mar. 7, 2006, all claiming the benefits of same named provisional patent application filed on Sep. 8, 2003 with China Patent Office.

With the improvement disclosed in these filings, every image point is specified by three color parameters derived from entire echo waveform, not just from the peak of the echo. Field points producing echoes of same peak amplitudes but different waveforms are effectively distinguished by different color compositions. Continuous medium body is presented in a color composition determined by the interfaces confining the medium. However, this improvement is still limited in the way that image points on the same sound path (same scan line) and confined by the same pair of interfaces are represented either identically, or in monotonically changing manner. In reality, the acoustic properties near the interfaces typically vary in a non-linear and non-monotonous manner, the closer to the interface, the more dramatic the acoustic variation is. Prior to the present invention, no effective means of charactering or imaging such acoustic conditions are commercially available.

Some very thin sheet targets, such as the blades of an aircraft engine or power generator operating at extremely high speed, while being most vulnerable to interior defects, are the hardest to inspect by conventional ultrasonic inspections, due to the simple fact that tiny echoes generated by defects are buried in much larger echoes contributed by the front and back exterior walls. Continuous defects that distort rather than reflect sound signals, are by far more harmiftl to thin targets than to thicker targets, but are even harder to detect.

The usefulness of any inspection is largely determined by its visual impacts to the operator. First, visual sense communicates with brain most efficiently. The information that a single glimpse sends to the brain, if to play out in audio frequencies, can take years of listening. In technical language, visual sense possesses a bandwidth significantly broader than other human senses do. Secondly, visual sense has unique spatial perception. Not only the existences of all the objects within the sight, but also the spatial attributes such as dimensions, shapes, relative positioning with each other, can be learned via visual sense almost instantly without training.

In terms of spatial perception and efficiency, visual presentations of all ultrasonic inspections are not equal. The best presentation is the stereoscopic real time images, such as a pumping heart, a breathing lung, or a live baby moving in mother's womb. Not surprisingly, this most desired presentation, known as four dimensional imaging, is produced by very expensive ultrasonic imaging systems.

On the other end, the numerical thickness readings presented by ultrasonic thickness gauges, although efficient in conveying measurement results, provide no spatial perception. A numerical reading is not visually related to the spatial attributes like size or spacing. "0.9999" and "1.0000" look very different but are practically equal, while "0.07" and "0.01" seem more alike but differ drastically. Many thickness gauges use a sound beep to alert the occurrence of pre-defined thickness reading, indicating that numerical readings alone can not fulfill the task satisfactorily. Moreover, in erosion inspection of extended pipelines or gigantic high pressure vessels, hundreds even thousands thickness measurements are needed to locate the worst erosion spots. In such common and demanding inspection tasks, an appropriate image is definitely better than piles of numerical readings.

Signal traces, always used but not necessarily explicitly displayed by all ultrasonic inspection equipments, carry valuable information not shown in numeric readings and traditional images. A false thickness reading, due to severe noises or overlap of multiple echoes, often can be identified from the signal trace. However, users are unable, or to larger extent, unwilling to deal with signal traces because of their poor visual image. It is a demanding task, even for well trained NDT professionals, to identify flaws through tiny echoes buried in much larger interfering echoes and background noises. Whenever possible, most inspectors rather take the straightforward numeric readings over insightful signal traces.

Ultrasonic erosion inspection and flaw detection are rarely performed by imaging systems despite of all the merits of image, not only because imaging systems are prohibitively expensive for typical NDT operation budgets, but also due to the operability limitations of imaging systems. Transducer arrays used in medical imaging can manage an adequate acoustical contact with soft human bodies, but not on rigid, curved surfaces and small facets, and are not practical when the test spots have narrow accesses, high temperature, or other severe conditions. Mechanical scan require good acoustic coupling between the transducer and target without changing target's positioning, which is achieved either by running a stream of coupling agent between the transducer and the target throughout the inspection, or by immersing the scan mechanism in a tank filled with coupling agent (water or oil)—not feasible for most NDT situations.

Above discussions indicate three much needed improvements in ultrasonic inspection: a) inspection or characterization for continuously distributed physical/acoustical conditions; b) inspection or characterization for very thin sheets; c) an inexpensive, practical way to generate visual images in ultrasonic erosion inspection, flaw detection and other common and demanding NDT tasks.

SUMMARY OF THE INVENTION

The objective of the present invention is to provide a combined solution to all three above discussed challenges that the prior art has failed to answer in decades.

The present invention discloses apparatus and methods of a new category of ultrasonic inspection with the following merits:
  a) Presentation wise, it possesses the efficiency and spatial perception of images, the straightforwardness and exactness of numerical readings, and the informational richness and insightfulness of signal traces.
  b) Hardware cost wise, it is in line with ultrasonic flaw detectors, and is significantly less expensive than ultrasonic imaging systems.
  c) Applicability wise, it works on any spots where traditional NDT flaw detection or erosion inspection can be performed.
  d) Functionality wise, it covers the traditional tasks of thickness gauging, flaw detection and significant part ultrasonic imaging, with drastically improved performance in characterization of thin sheets with or without interior discontinuities—the most challenging task in ultrasonic inspection.
  e) Operation wise, the intuitively understandable visual presentation, and the significantly reduced rate of false detection and failed detection, making ultrasonic NDT significantly easier and preferable.

DETAILED DESCRIPTION OF THE INVENTION

This invention discloses methods and apparatus for ultrasonic color imaging that characterizes ultra-fine structures and distributional physical conditions within the target under inspection. The disclosed method complementarily incorporates information arising from a plurality of repeated sound trips forced by repeated reflections of exterior and interior interfaces of target, and visualizes the information into an image segment representing the main path that ultrasonic signals have traveled within the target. An image that is substantially more discriminative, descriptive, and position-sensitive to both acoustic interfaces and distributional acoustic characteristics of the target, is achieved as the result.

The invention is especially useful for thin sheet targets most vulnerable to both non-continuous and continuous interior defects. The continuous interior conditions and effects of ultra-thin layered structures are effectively expressed in color image details.

The ultrasonic color imaging method of present invention deals with trace of ultrasound signals that repeatedly travel on same main path due to multiple reflections of exterior and interior interfaces of the target. The processes include: a) preparing an array of sequenced numerical data substantially rooted from said trace of ultrasound signals; b) selecting a plurality of data members from the array of sequenced numerical data such that selected members were respectively and effectively influenced by same geometric position on the main path during different repeated trips; c) calculating a plurality of color parameters from the selected data members, to express said geometric position on said main path into an image element of a color image; d) for each and every geometric positions on the main path, performing b) and c) to express the overall trace into an image segment representing entire main path within the target.

The process of deriving the array of sequenced numerical data can be chosen from the following: digitization of the trace without substantial modification; Fourier transforms of the trace; inverse convolutions or de-convolutions using the trace as a source function; digital signal processing for suppressing background noises, for emphasizing contributions of pre-selected physical effects imposed by said target, and for separating contributions among repeated sound trips; combinations of above processes.

The image segments of many traces covering different main paths across same target are arranged to form a cross-sectional profile of the target.

The image segment representing an entire path within the target is composed of parallel color lines. The spacing between the two edge lines is proportional to the target thickness as measured at the location where the trace was recorded. The relative position of each color line with respect to the two edge lines stands for the geometric point on the main path with same relative position with respect to two target surfaces. The color composition of each color line represents how the corresponding geometric point affects the passing-by ultrasound signals in consecutive repeated trips.

The color composition of the edge line representing front wall of the target may be defined by:

$$RGB(F_{01}(y_{T_0}, y_{T_1}, y_{T_2}, \ldots),$$

$$F_{02}(y_{T_0}, y_{T_1}, y_{T_2}, \ldots),$$

$$F_{03}(y_{T_0}, y_{T_1}, y_{T_2}, \ldots))$$

and the color composition of other lines may take a general form of:

$$RGB(F_1(y_{T_1-i}, y_{T_2-i}, y_{T_3-i}, \ldots),$$

$$F_2(y_{T_1-i}, y_{T_2-i}, y_{T_3-i}, \ldots),$$

$$F_3(y_{T_1-i}, y_{T_2-i}, y_{T_3-i}, \ldots))$$

where RGB(Red, Green, Blue) stands for a system-supported function defining display color by three color parameters for the amounts of Red, Green and Blue respectively. $F_{01}$ and $F_1()$, $F_{02}$ and $F_2()$, $F_{03}$ and $F_3()$ are multi-variable functions in different forms, for calculating Red, Green and Blue parameters respectively. i stands for the time needed for sound to travel a round trip between the position that the line stands for and the back wall of the target. $T_0$ is the time moment of the first front wall echo, and $T_1$ through $T_n$ are time moments of first through nth back wall echoes respectively.

$y_{T_n}, y_{T_1-i}, y_{T_2-i} \ldots$ are dada members in the array of sequenced numerical data corresponding to $T_n, T_1-i, T_2-i$ respectively.

The ultrasonic apparatus disclosed by present invention comprises of: a setup of launching a detecting ultrasonic signal into a target under inspection; a setup of retrieving the trace of ultrasonic signals resulting from the interactions between the detecting ultrasonic signal and the target; a setup of digitizing the retrieved trace and preparing an array of sequenced numerical data substantially representative of the digitized trace; and a setup of color imaging, which further comprises of: a) selecting a plurality of data members from the array of sequenced numerical data, the selected data members were respectively and effectively influenced by a given geometric position on the main path during different repeated sound trips; b) calculating a plurality of color parameters from the selected data members to express that given geometric position into an element of a color image; c) repeating a) and b) for all geometric positions on the main path so that the overall trace is expressed into an image segment representing the entire main path within the target.

Launching detecting signals into the target, retrieving the resulting signal traces, digitizing signal trace into digital form, processing the digitized trace into sequenced data arrays with different mathematic methods, etc., all are typical elements in the prior art that build the platform for the present invention. The core of present invention is using a sequenced data array to generate a color image segment containing the information related to multiple repeated sound trips on the same sound path, while the prior art generates a gray-scale image segment containing only the information of a single sound trip on the same path. Any skilled C++ programmer knowing how to work with data arrays and how to draw color lines connecting a pair of geometric points can implement the present invention on the platform of a prior art ultrasonic inspection device.

It is a major objective of the present invention to provide new tools of producing desirable image presentation for common NDT operations without the high costs and operability limitations of traditional ultrasonic imaging. This goal is achieved by the disclosed ultrasonic apparatus which allows taking image segments at operator's will without restrictions. The image segments are not arranged according to the relative geometric positions of corresponding main paths. Instead, the obtained image segments are displayed in sequential order of trace taking operation, unless the operator wants otherwise. The resulted cross-sectional profile does not comply with rules of traditional imaging, but well serves the purpose of comparing obtained image segments to identify abnormal interior condition—exactly what the present invention wants.

The disclosed ultrasonic apparatus also supports: storing a predetermined number of signal traces; a movable cursor allowing the operator to highlight any image segment in the displayed profile to bring up the additional information associated with the highlighted segment, including: entire or a selected portion of corresponding signal trace, an array of sequenced numerical data rooted from the trace, thickness reading and other numeric quantities characterizing the signal trace, numeric quantities characterizing all stored traces as a group, the information display is independent of the main display—the cross-sectional profile composed of many segments for the operator to choose. In such a way, the apparatus performs the functionality of thickness gauging, flaw detection, and other inspection tasks. The cross-sectional profile serves a visual organizing and accessing tool for all information available from all stored signal traces.

Preferred Embodiments (1) An Embodiment Based on Signal Trace

Figure 1:
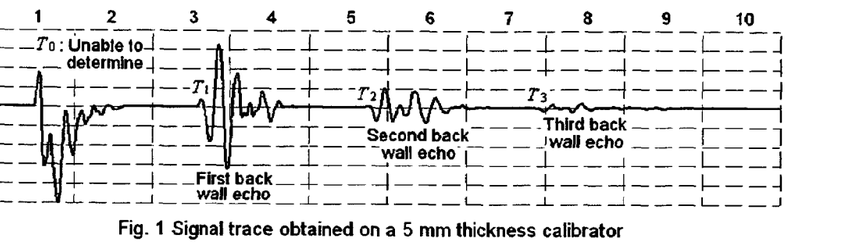
FIG. 1 illustrates the signal trace generated by a 5 MHz transducer on a 5 mm thick calibration block.

FIG. 1 shows the signal trace generated by a 5 MHz transducer on a 5 millimeter thick calibration block (the target). The echo in third and fourth divisions is the first back wall echo. The second back wall echo occupies divisions 5 and 6. The third back wall echo spans divisions 7 through 9. The waveform in first and second divisions is the triple superposition of electrical excitation impulse, acoustic excitation signal, and the front wall echo. It is impossible to tell the three apart from each other. Without a clean front wall echo, target thickness d can be determined by the spacing between the first and second back wall echoes. In the following we present three different images, all based on the same trace shown in FIG. 1.

a) The image segment generated by traditional ultrasonic imaging, so called B-image (Brightness image), is composed of two bright line segments parallel with each other in black background, representing two exterior walls of the target. With the front wall echo not available, the line segment representing front wall is given a fixed brightness value, say 255. The line segment representing back wall is displayed with a brightness proportional to the peak amplitude of first back wall echo. In the trace of FIG. 1, that is 0.62*255=158. The spacing between the two line segments represents the target thickness at the location where the trace was recorded. If the display resolution is 5 pixels per millimeter, then the spacing is 25 pixels, indicating a thickness of 5 millimeter.

b) The image segment generated by the color imaging method prior to the present invention, disclosed in U.S. patent application Ser. No. 11/369,603 by present inventor, is composed of two color line segments in white background. The positioning and spacing of two line segments are the same as the brightness image. Again, without front wall echo waveform, the front wall is assigned a reference color, say RGB(255, 255, 255). The meaning of RGB( ) function is covered in the discussion of color parameter in VOCABULARY AND DEFINITIONS. The back wall color is defined by RGB($x_1$, $x_2$, $x_3$), where $x_1$, $x_2$ and $x_3$ are three color parameters derived from the waveform of the first back wall echo. For simplicity, we relate them to the amplitudes of three largest lobes of echo waveform. Obviously, color image based on three parameters responds to waveform distortion therefore discriminates more material conditions than one parameter based brightness image which responds only to amplitude reduction. The space between the two edge lines can be filled with color RGB(255–$x_1$, 255–$x_2$, 255–$x_3$).

c) The image segment generated by a trace-based embodiment of present invention looks quite similar to the above case. Nevertheless, with information of three back wall echoes to be incorporated into the image, the image of back wall can be much more insightful. According to the reflection theory, the waveform distortion before and after reflection relates to the reflection characteristics of the interface. Only a perfect reflection makes no change to waveform. The waveform distortion can be implemented into the image as follows:

Suppose $A_1, B_1, C_1$ stands for amplitudes of three largest lobes of first back wall echo. Similarly, $A_2, B_2, C_2$ are corresponding parameters for second back wall echo, and $A_3$, $B_3$, $C_3$ for the third back wall echo. Here the subscriptions indicate which echo the parameter belongs to. The color composition of back wall is implemented as RGB(X, Y, Z), where $$X=255*(A_2/A_1);$$

$$Y=255*a*(2*(A_2/A_1)-(B_2/B_1)-(C_2/C_1));$$

$$Z=255*b*(2*(A_3/A_2)-(B_3/B_2)-(C_3/C_2));$$

For a perfect reflection, the ratio of corresponding parameters between two echoes should be all identical, i.e. $A_2/A_1=B_2/B_1=C_2/C_1$, and $A_3/A_2=B_3/B_2=C_3/C_2$, therefore Y=Z=0. Since X is the amount of Red composition, the image color of back wall is pure red. The intensity of red color is proportional to $A_2/A_1$, the reflection ratio or reduction of signal size. That is, in the case of perfect reflection, this embodiment of present invention and the traditional B ultrasonic imaging are essentially identical. However, when faced with real life, imperfect reflections by imperfect interfaces, the multiple-echo-based color imaging of present invention can quantitatively describe the imperfections via color parameters Y and Z, while the traditional imaging pretends the imperfections don't exist. Constant factors a and b can be adjusted to emphasize or de-emphasize the effects of second and third echoes respectively. This embodiment is only one of numerous possibilities enabled by imaging an interface with three echoes instead of a single parameter from a single echo.

The greatest merit of basing imaging on signal trace is easy to implement. The negative side, however, is well demonstrated by the signal trace in FIG. 2, where echoes from front and back walls are all overlapped together, no analysis and measurement is possible without major advances in analyzing methods or tools. That is the determining factor of introducing the next embodiment.

(2) An Embodiment Based on Acoustic Impulse Response of Target

It was a major goal of present invention to provide a characterization tool for continuous acoustic medium body, especially the medium in thin sheet or near interior interfaces and exterior boundaries. Such new capability should be achieved to complement, not to compromise the existing capability of detecting interfaces or discontinuities. This goal is successfully realized by a preferred embodiment based on acoustic impulse response of target.

Figure 2:
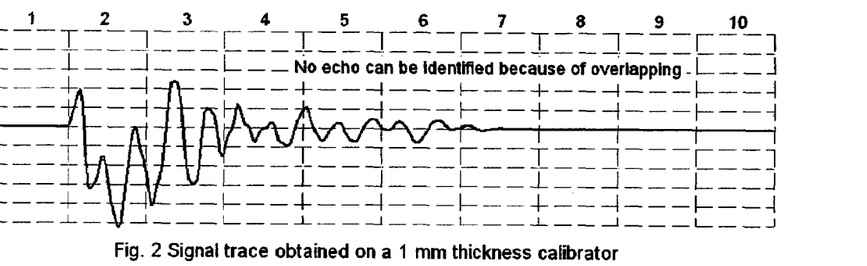
FIG. 2 illustrates the signal trace generated by the same 5 MHz transducer on a 1 mm thick calibration block.

FIG. 2 shows the signal trace generated by a 5 MHz transducer on a 1 millimeter thick calibration block. The waveform dramatically differs from the one in FIG. 1, not only because of the overlap among echoes, but also because of the waveform change of each individual echo. For a target in 1 mm thickness range, the distribution of acoustic properties is dominated by surface effects as a function of distance from target surface. The non-monotonous nature in acoustic properties dramatically reshapes the waveform of passing-by sound signals even without any discontinuities. The present invention effectively incorporates the waveform reshaping characteristics of a target into a cross-sectional image, revealing variation of acoustic properties as a function of depth from the target surface.

A signal trace is dominated by two primary factors: a) the transducer characteristics independent of target; b) the accumulated acoustical effects of the sound path within the target. In the case of a thin sheet target, the main path is traveled multiple times. Since the purpose of ultrasonic NDT is inspecting the target, not the transducer, it is highly desirable to separate the target (the sound path) effects from the transducer effects. An effective way of achieving such separation is deriving the impulse response of the sound path from the trace.

Impulse response plays a center role the linear filter theory—a foundation of digital signal processing. When an input signal goes through a system (such as a target under inspection), the signal waveform experiences a specific reshaping process determined by the characteristics of the system. The resulting output signal can be expressed, to the extent of linear approximation, as the mathematic convolution of the input waveform and the impulse response of the system. Technically, if the waveforms of input signal and output signal are both known, the impulse response of the system can be calculated via inverse convolution (de-convolution) or Fourier analyses. Accordingly, if the signal waveform before entering the target and the signal trace are known, the impulse response of the target can be computed. There have been plenty of publications on computing impulse response of a system from the input and output signals. Finding a generic way of computing impulse response from signal trace for widely diverse applications has not been fruitful. It was not an objective of present invention to provide methods of obtaining impulse response from signal trace. Rather, the present invention focuses on utilizing a signal trace, an impulse response, or other sequenced data collections rooted from a signal trace to produce cross-section color profiles best characterizing the target.

Figure 3:
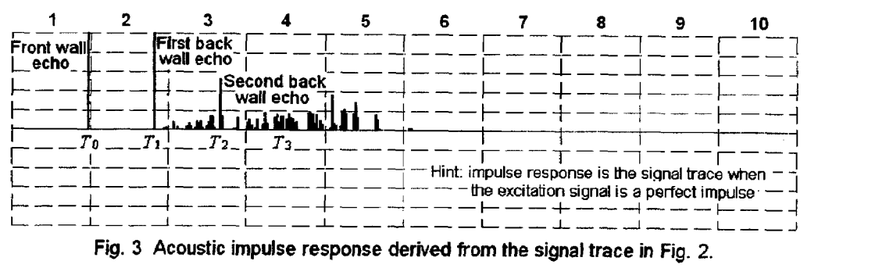
FIG. 3 illustrates an impulse response derived from the signal trace in FIG. 2. Impulse response is actually the signal trace when the excitation signal is a perfect impulse.

FIG. 3 shows an impulse response derived from the trace in FIG. 2. When computed properly, the impulse response of a complete sound path tells the exact timing of each reflection (therefore the exact location of each interface), as well as how the waveform is altered by each reflection. By theory, only a perfect reflection generates an echo perfectly replicating the incident signal. The impulse response of a perfect reflection is a single vertical line of unity height standing on time axis at a location representing the timing of the reflection. Since there is no such thing as perfect reflection in real life, reflections encountered in NDT inspections typically have an impulse response of a tall vertical line surrounded by several leading and trailing short lines, as can be seen in FIG. 3. The cleanliness of the impulse response directly represents the pureness of the reflection. The interior scattering, attenuation, diffractions, side wall reflections, roughness and incident angle relative to the interface, etc., all contribute to the waveform reshaping (including but not limited to size reduction) and showing their effects in the signal trace. The impulse response derived from a trace characterizes acoustic effects much better than the trace itself does, because the interfering effects of transducer in the trace have been eliminated, at least significantly reduced.

The preferred embodiment utilizes impulse responses calculated from the signal trace to minimize the transducer effects before thickness and flaw analysis. Unavoidably, the quality and performance of the transducer still play a role through affecting the accuracy of obtained impulse response. However, the transducer characteristics impact the trace much more significantly and unpredictably than they impact the computation of impulse response. The impulse response approach is most advantageous for thin targets generating multiple, overlapped echoes, a nightmare of traditional ultrasonic NDT for decades.

Figure 4:
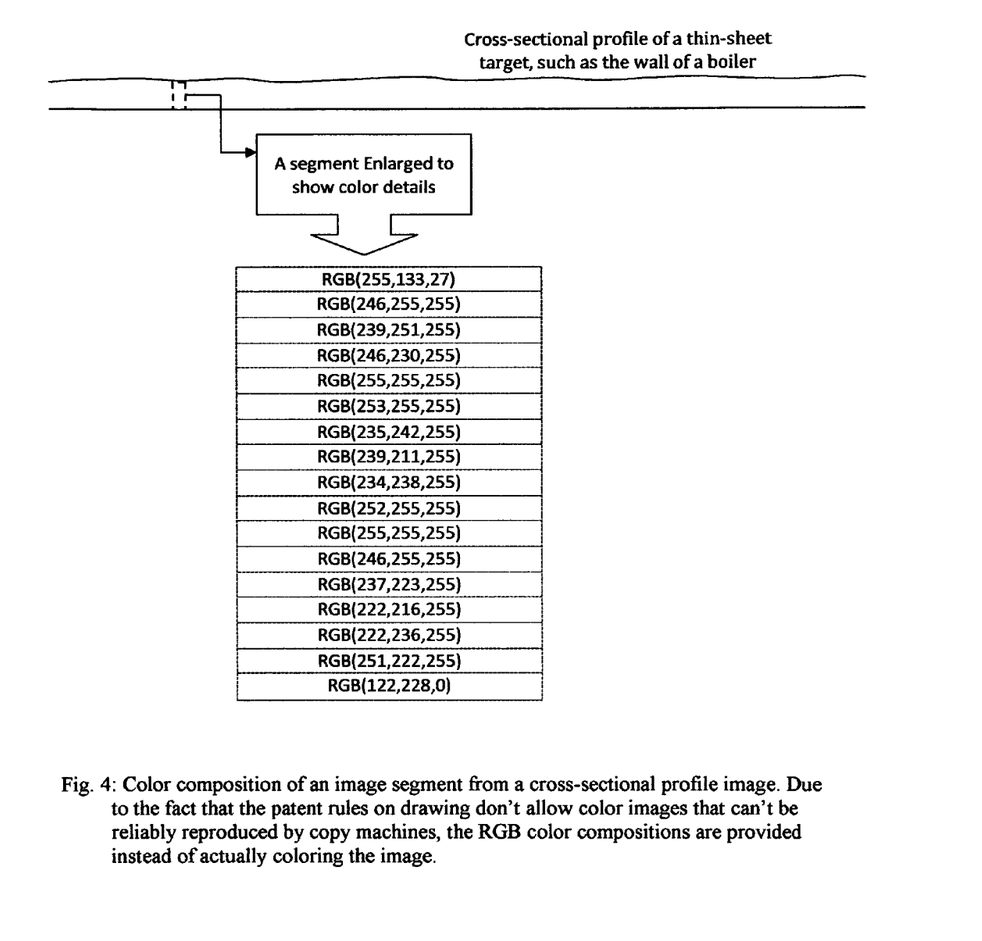
FIG. 4: illustrates the color composition of an image segment taken from a cross-sectional profile image. Due to the fact that the patent rules on drawing don't allow color images that can't be reliably reproduced by copy machines, the RGB color compositions are provided instead of actually coloring the image.
Figure 5:
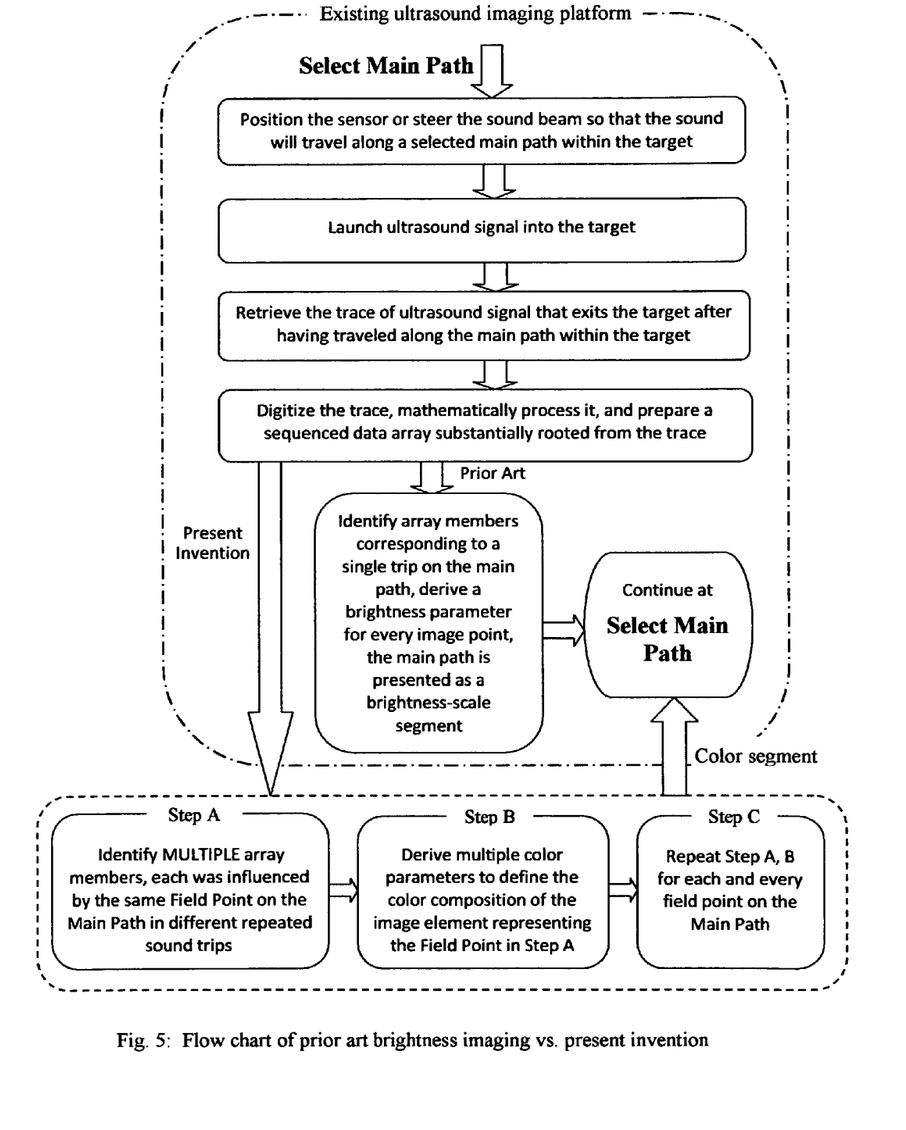
FIG. 5 illustrates how the present invention compares with the prior art imaging in flowchart presentations.
Figure 6:
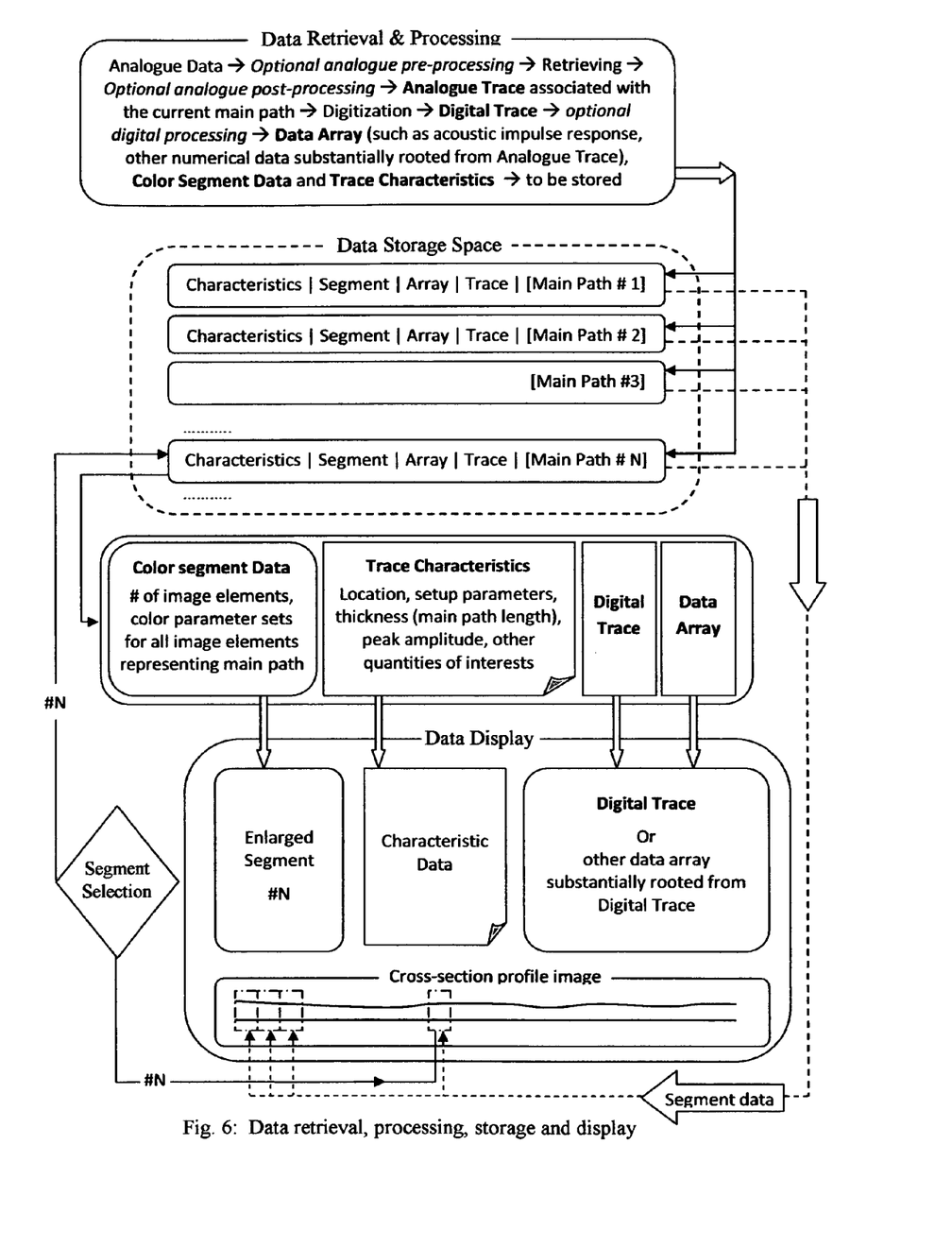
FIG. 6 illustrates the data retrieval, processing, storage and display of a preferred embodiment.

FIG. 4 shows a cross-sectional profile image produced by a preferred embodiment. The profile is composed of a number of side-by-side color segments. Each segment is further composed of a stack of equal sized color straps. One of the color segments is enlarged to demonstrate how the present invention differs from the gray-scale, prior-art ultrasound imaging that fills the segment with a brightness either un-varying, or monotonically varying between the opposite boundaries.

The height and width of all color straps remain unchanged for entire image, and are solely determined by the vertical and horizontal image resolutions (object-size per pixel) respectively. The target thickness at the spot where the signal trace was retrieved is proportional to the total height of all straps in the stack, and determines the number of straps in the segment. Every color strap is filled with a color composition defined by a set of color parameters exclusively assigned to this strap. In such a way, the variations in composition and physical-property, either along the target surface or across the target depth, are effectively presented via color variations. Any unusual material conditions, whether continuous or discontinuous, can cause dramatic changes in the color pattern of the corresponding segment, draws attentions from the operator.

The thickness is the most critical information in forming an image segment, must be determined as the first step. Let's use FIG. 3 to show the process of a preferred embodiment. The first vertical line in black stands for the reflection by the front wall. The highest blue vertical line stands for the first reflection by the back wall. Let T be the horizontal distance between the black line and highest blue line, it then represents the time needed for sound to travel a round trip between the front and back walls. With T known, thickness d at the test spot can be readily calculated by $d=0.5\ T*v$, where v is the sound speed of the target material, factor 0.5 counts for the fact that T is the time for a round trip.

Traditionally, T is determined from the trace. Drawing T from an impulse response is easier and much more reliable. In fact, a trace works only when the target is thick enough so that the echoes generated by front wall and back wall are clearly separated from each other, as the case in FIG. 1. The thinner the target gets, the smaller the separation between adjacent echoes becomes, until the echoes overlap on each other. When this happens, more sophisticated methods, such as impulse response, frequency analysis, etc. have to be employed to correctly determine the time intervals between the overlapped echoes. As declared earlier, the present invention does not provide the method of computing impulse response from a trace, rather, it covers a method of producing color cross-sectional profile from a known impulse response.

Once T, the time period needed for sound to travel a round trip between the two exterior surfaces, is correctly determined, the location of all echoes corresponding to multiple reflections can be easily calculated. Let $T_0$ be the time moment at which the front wall reflection takes place, $T_1$, $T_2$, ... $T_n$ be the time moments of the $1^{st}$, $2^{nd}$ and the nth reflection by the back wall, the following relation applies:

$$T_i = T_0 + i*T \quad i=1,2,\ldots n \qquad \text{Eq. (1)}$$

This relation holds both for signal trace and impulse response.

The multiple reflections in a trace provide a rich information resource about the acoustic conditions of the target. The information is inherited by mathematical transforms rooted from signal trace, such as the impulse response, Fourier transform, etc. The process described here applies to other mathematical transforms.

Impulse response is actually a special case signal trace,— the trace obtained with an ideal transducer generating a spike-shaped signal waveform with no leading or trailing ringing. The better the transducer signal can be approximated by an impulse, meaning the front wall echo has narrow and high main lobe with few and small ringing, the more accurately the impulse response can be derived from the signal trace.

In the impulse response in FIG. 3, $T_0$, the timing of the front wall echo is the horizontal location of the black line, and $T_1$, the timing of the first back wall echo is the horizontal location of the highest blue line. T, the time period for sound to travel a round trip between the front and back walls of the target, is calculated by $T=T_1-T_0$. With T and $T_0$ known, $T_2$ through $T_n$ are calculated by Eq. (1). In software implementation, $T_0$ through $T_n$ are integer indexes of an integer array allocated for storing the impulse response.

The segment height stands for target thickness at the spot where the trace was obtained. It is proportional to T. Suppose T equals N sample intervals, the segment is then composed of N+1 horizontal color lines of equal width. The top and bottom lines represent the front and back walls, with color composition determined by data value at locations $T_0$ through $T_n$, i.e. the heights of vertical lines at locations $T_0$ through $T_n$ in FIG. 3. Let us denotes them by $y_{T_0}$ through $y_{T_n}$.

The color composition of top edge of profiles in FIG. 4 was implemented as $$RGB(y_{T_0}, y_{T_0}-y_{T_1}, y_{T_0}-y_{T_2}) \qquad \text{Eq. (2)}$$

While the composition of bottom edge was defined as $$RGB(y_{T_1}, y_{T_2}, y_{T_3}) \qquad \text{Eq. (3)}$$

It is important to understand that $y_{T_1}$, $y_{T_2}$, $y_{T_3}$, although representing reflections taking place with clearly separated timing, are attributable to same target point—the back wall spot that intersects with the sound path. By Eq. (2) and (3), the top edge color composition is dominated by the front wall echo $y_{T_0}$ while the bottom edge color gives equal weights to first three back wall reflections $y_{T_1}$, $y_{T_2}$, and $y_{T_3}$. Expressions in Eq. (2) and (3) can be freely redefined to shift the emphases from one reflection to another to address different application purposes.

Expression (2) seems a little fancy than it needs to be. There is a reason for it. In ultrasonic inspection practice, a signal trace not only depends on target and transducer, but also strongly depends on acoustical coupling between the transducer and the target. In other words, the outcome of inspection can strongly depends on how the inspector holds the transducer on the target surface. By Eq. (2), the image of the top line strongly dependents on $y_{T_0}$, the front wall signal, therefore is sensitive to the coupling, providing an convenient way for checking the coupling consistence.

A line in the middle of top and bottom lines with a distance i from the bottom, is implemented to have a color composition $$RGB(y_{T_1-i}, y_{T_2-i}, y_{T_3-i}), i=1,2,\ldots N-1. \qquad \text{Eq. (4)}$$

By running i from 1 through N−1, all the color lines in the segment are individually defined by three data members in the impulse response. Again, $y_{T_1-i}$, $y_{T_2-i}$, $y_{T_3-i}$, although with different timing in different round trips, are equally distanced from $T_1$, $T_2$, $T_3$ respectively, therefore describe the same geometric point in the target body. Data members from different trips can be incorporated in describing a single image point as long as these data members are attributable to the same corresponding field point. Consider a crack located at i sample intervals from the back wall, causing extra reflections at time moments $T_1-i$, $T_2-i$, $T_3-i$, i.e., causing $y_{T_1-i}$, $y_{T_2-i}$, $y_{T_3-i}$ to be much larger than their neighbors, resulting the ith color line counting from bottom to be significantly darker than other lines. If $y_{T_1-i}$, $y_{T_2-i}$, $y_{T_3-i}$ were applied to other field points, more than one line would be wrongfully strengthened, suggesting more than one cracks.

As an ultrasound signal travels within the target body, the waveform reshapes itself and signal amplitude decreases along the way. Echoes of higher reflection order, say second or third echoes, travel longer distance, interact with more target interior therefore carry richer information about the target interior. The negative side is that echoes of higher orders are contaminated by more noises and other unwanted interferences. The preferred embodiment gives operator an option of weighing the reflections of different orders differently for different application needs. Expression (4) can be generalized as $$RGB(F_1(y_{T_1-i}, y_{T_2-i}, y_{T_3-i}, \ldots),$$

$$F_2(y_{T_1-i}, y_{T_2-i}, y_{T_3-i}, \ldots),$$

$$F_3(y_{T_1-i}, y_{T_2-i}, y_{T_3-i}, \ldots))) \; i=1,2, \ldots N-1. \qquad \text{Eq. (5)}$$

where $F_1()$, $F_2$, $F_3()$ stand for three different multi-variable functions for calculating the Red, Green and Blue parameters in RGB color system. By changing the definition of $F_1()$, $F_2$, $F_3()$, sectional profiles emphasizing different interior characteristics can be achieved.

Let's use the acoustic impulse response in FIG. 3 to exemplify how a color segment is processed.

Suppose the acoustic impulse response in FIG. 3 is stored in data array y[ ] containing 400 data members. The $39^{th}$ and $72^{nd}$ data members have data values much more significant than others, representing the amplitudes of the reflection by the front wall and the first reflection by the back wall respectively. $T_0$, the timing of the front wall reflection therefore is 39, while $T_1$, the timing of the first back wall reflection is 72. T, the time period for sound to travel a round trip between the front and back walls, is 72−39=33 (equals the total time taken for collecting 33 data samples). Using Eq. 1, $T_2$ and $T_3$ can be readily calculated as 105, 138 respectively. The amplitudes of the corresponding reflections are found in data members y[39], y[72], y[105], and y[138]. The color composition of the top edge of the segment can be calculated by plugging y[39], y[72], y[105] in Eq.2. Similarly, the color composition of the line right below the top edge is obtained by inserting y[40], y[73], y[106] in Eq. 4. Then, y[41], y[74], y[107] are put in Eq. 4 for the next line . . . until the bottom line in the segment is reached, which has a color composition defined by RGB(y[72], y[105], y[138]). The information of multiple reflections (after being transformed into the impulse response) is thus incorporated into a color segment of a sectional profile.

The interior scattering, attenuation, diffractions, side wall reflections, roughness and incident angle relative to the interface, etc, all contributed to the size reductions and waveform reshaping of the signal trace recorded. The present invention provides an effective way of incorporate all these acoustical effects into a single cross-sectional segment. If interior conditions underneath certain inspection spots have changed because of material fatigue, strain damages, temperature gradations, physical strikes, prolonged exposure to physical or chemical effects, etc, the color image of the corresponding segment will differ from that of other segments, revealing the location, as well as many details of the condition changes.

By linking the segment image to a front wall echo and several back wall echoes, a single color image brings out by far more interior characteristics than traditional, one-echo-based ultrasonic imaging. The resulting cross section profile is by far more discriminative and sensitive to tiny variations, as well as to their geometric distributions inside the target. Whether the variations are abrupt or gradual, near to or far away from the exterior walls, constructively or destructively overlapped, as long as there are any waveform reshaping effects, the preferred embodiment can show them in the cross-sectional profile image.

The traditional imaging complies with rules of positioning, proportioning and completeness, i.e., each image element (a pixel or a group of pixels) must be placed at the right position with respect to other image elements, with consistent proportion, and the entire target body within the scope is imaged without omission. When a transducer array or a computer automated mechanic scanning system is use, scan parameters such as scan routes and scan steps, are used both for scan control and for image construction, automatically assures positioning, proportioning and completeness. A controlled scan mechanism has always been an integral part of the traditional ultrasonic imaging.

The preferred embodiment imposes no restriction on selection of inspection spots. In the default display mode of Cross Sectional Profile, a new segment is place to the right of existing profile for every new trace obtained at a new spot. Any spots can be visited at any time regardless of positioning, proportioning and completeness. The inspection spots can be scattered in any direction with any spacing; can be tested/re-tested in any order; can be clearly separated from or overlapped with each other; can be on the same smooth surface or on different facets of a target, even on different sub-targets. A profile image composed of segments taken at such un-regulated spots, although untraditional, but serves NDT purpose even better.

In NDT applications, more often than not, the real purpose is detecting abnormal or potentially harmful spots rather than pursuing a complete interior image of the target. How the underneath of a target spot materially compares with other portions of target is often more important than the actual visual appearance of the spot. The preferred embodiments provide a visual presentation concentrating on detecting abnormal from normal, rather than on pursuing rigorousness and completeness of the imaging process. The reward of losing traditional sense of image is achieving the flexibility not allowed by traditional imaging systems, as well as the visual advantages not possessed by flaw detectors.

Erosion inspection of large scale equipments is a major application targeted by the present invention. Consider a large chemical vessel with its wall thickness varying between 0.95 through 1.05. Although a fluctuation less than 10%, the updates of thickness readings in the display window of a thickness gauge keep operator's eyes and mind busy and wearing out. When a really alarming reading 0.35 does appear, its visual impact is no more that the impact of 0.95. Only if the beep alarm is active and alarm threshold has been set properly, a sound alert can be issued to save the visual incompetence. Alternatively, the preferred embodiment displays a series of side-by-side profile segments separated by a narrow vertical blank. The height of a segment is proportional to the wall thickness of the corresponding test spot, visually and straightforwardly shows how the wall thickness varies with the test spots. Without any knowledge about thickness range and threshold setting, without unnecessary nerve striking and vision fatigue, the embodiment not only catches the occurrence of a serious event, but also tells how serious the event is with all the advantages of human vision—effectiveness, efficiency and spatial perception. Beep alarm is still in use, but not triggered by a pre-defined threshold setting, but by image contrast between the new segment and other existing ones.

There are some other aspects in the processing of cross-sectional profile. They are addressed or implemented by the preferred embodiment as follows:

The width of segment is determined by the total display width and the number of segments being displayed. In principle, the image out of every amplitude response should be a single pixel wide, i.e. a vertical line in the profile. In practical applications, single pixel wide image piece is not visually perceived well, therefore is artificially expanded horizontal-wise. The minimum and maximum segment width should be predefined and applied. For example, the minimum segment width can be set as 1/50 of display width, and the maximum segment width is set as 1/10 of display width respectively. Say the total display width is 200 pixels, the minimum and maximum segment widths are 4 pixels and 20 pixels respectively. The maximum number of displayed segments is then 50. The first segment in the window uses the maximum segment width, 20 pixel-wide in this case. As the inspection continues and the number of segments increases, the widths of all displayed segments decrease gradually until the minimum segment width is reached. After the total number of displayed segment reaches 50, any newly added segment will push the segment on the left end out of the window, the segment width is kept at 4 pixels wide and the total number of displayed segments remains 50. A horizontal sliding bar can be implemented to move the displayed portion of cross-sectional profile to bring the segments that have been pushed out of the window back to the scene.

The vertical scale of display is determined by the maximum depth or thickness of the application. As an example, say the vertical display size is 100 pixels high, the maximum thickness is set at 1 inch, the vertical scale or the thickness resolution is then 100 pixels per inch. A target of 0.01 inch thick will be displayed as one pixel high. Several ways were implemented to address vertical resolution related issues: a) The operator can horizontally move a cursor to highlight any displayed segment (make it current), the exact thickness reading of the selected segment will be displayed as numeric reading at a window location allocated for thickness readings of current segment. b) Reset the vertical scale for better vertical resolution, say 400 pixels per inch. In cases vertical overflow of some thick segments, a vertical sliding bar can be used to move the display vertically to show the overflowed part. c) An display mode that dynamically resets the vertical scale according to the largest thickness of all segments being displayed. The vertical resolution X pixels/inch (or mm) is automatically updated at a dedicated window location.

The placement of new segment: By default, the latest segment is added to the right end of the cross-sectional profile. The very first segment in an empty window can be placed either at the left side of the window or any location at user's choice. A segment cursor can always be moved along the cross-sectional profile to make any segment or segment slot current, brings up detailed information about the current segment, or fill the current segment slot with next available segment image. The usage of segment cursor is implemented similarly to the cursor in PC based word processing software that allows user to add or insert a new letter anywhere.

The alignment reference: Alignment mode is one of the image presentation settings. Segments can be aligned either with the front or the back wall of the target. For most applications, such as erosion inspection, it makes more sense to align with the flatter, smoother front (exterior) wall, because the thickness variation is caused by erosion on the back (interior) wall. On the other hand, if the target has flat back wall, such as a calibration block with steps of different heights, using back wall as alignment reference is the obvious choice.

Orientation of profile display: Cross-sectional profiles shown in FIG. 4 are horizontally oriented. There is a Profile Orientation setting in the preferred embodiment that allows switching between horizontal and vertical profile presentation.

The invention claimed is:

1. An ultrasonic color imaging method to be applied with an ultrasound apparatus, comprising:
   a) accessing a trace of ultrasound signals provided directly or indirectly by said ultrasound apparatus, wherein said trace covers repeated trips of said ultrasound signals on a same main path within a target, and said repeated trips were forced by multiple reflections of exterior and interior interfaces of said target, wherein said ultrasound apparatus further performs the steps of:
   b) preparing an array of sequenced numerical data substantially rooted from said trace of ultrasound signals,
   c) selecting a plurality of data members from said array of sequenced numerical data such that selected data members were respectively and effectively influenced by same geometric position on said main path during different repeated trips of said ultrasound signals, and
   d) calculating a plurality of color parameters from said selected data members to express said geometric position on said main path into an image element of a color image,
   whereby the information arising from a plurality of said repeated sound trips is complementarily incorporated into the color image such that the color image is substantially more discriminative, descriptive, and position-sensitive to distributional acoustic characteristics of said target.

2. The ultrasonic color imaging method of claim 1, wherein steps c) and d) are repeated for all geometric positions on said main path so that overall said trace is expressed into an image segment representing entire said main path within said target.

3. The ultrasonic color imaging method of claim 2, further comprising:
   combining said image segments of said traces respectively covering different said main paths across said target to form a cross-sectional profile of said target.

4. The ultrasonic color imaging method of claim 2, wherein said image segment representing entire said path within said target is composed of parallel color lines, the spacing between two edge lines is proportional to the target thickness at the location where said trace was obtained, the relative position of each color line with respect to two edge lines stands for the geometric point on said main path with same relative position with respect to two target surfaces, the color composition of each color line represents how the corresponding geometric point within said target affects passing-by ultrasound signals in consecutive repeated trips.

5. The method of claim 4, wherein the color composition of the edge line representing front wall of said target is defined by:

$$RGB(F_{01}(y_{T_0}, y_{T_1}, y_{T_2}, \ldots),$$

$$F_{02}(y_{T_0}, y_{T_1}, y_{T_2}, \ldots),$$

$$F_{03}(y_{T_0}, y_{T_1}, y_{T_2}, \ldots))$$

and the color composition of other lines may take a general form of:

$$RGB(F_1(y_{T_1-i}, y_{T_2-i}, y_{T_3-i}, \ldots),$$

$$F_2(y_{T_1-i}, y_{T_2-i}, y_{T_3-i}, \ldots),$$

$$F_3(y_{T_1-i}, y_{T_2-i}, y_{T_3-i}, \ldots))$$

where RGB(Red, Green, Blue) stands for a system function defining display color by three color parameters quantifying the amounts of Red, Green and Blue respectively; $F_{01}$ and $F_1()$, $F_{02}$ and $F_2()$, $F_{03}$ and $F_3()$ are multi-variable functions in different forms, for calculating Red, Green and Blue parameters respectively; i stands for the time needed for sound to travel a round trip between the position the line stands for and the back wall of said target; $T_0$ is the time moment of the first front wall echo, and $T_1$ through $T_n$ are time moments of first through nth back wall echoes respectively, $y_{T_n}$, $y_{T_1-i}$, $y_{T_2-i}$ ... are dada members within said array of sequenced numerical data corresponding to $T_n$, $T_1-i$, $T_2-i$ respectively.

6. The ultrasonic color imaging method of claim 1, wherein said preparing process of said array of sequenced numerical data is selected from a group comprising: digitization of said trace without substantial modification, Fourier transforms of said trace, inverse convolutions or de-convolutions using said trace as a source function, digital signal processing for suppressing background noises, digital signal processing for emphasizing contributions of pre-selected physical effects imposed by said target, digital signal processing for separating contributions among repeated sound trips, and combinations thereof.

7. An ultrasonic apparatus comprising:
 a setup for launching a detecting ultrasonic signal into a target under inspection,
 a setup for retrieving a trace of ultrasonic signals resulting from interactions between said detecting ultrasonic signal and said target, wherein said interactions include repeated sound trips on same main path caused by repeated sound reflections by exterior and interior interfaces of said target,
 a setup for digitizing said retrieved trace and preparing an array of sequenced numerical data substantially rooted from the digitized trace, and
 a setup for color imaging, comprising:
  a) a setup for selecting a plurality of data members from said array of sequenced numerical data such that selected data members were respectively and effectively influenced by a given geometric position on said main path during different repeated trips of said detecting ultrasound signal,
  b) a setup for calculating a plurality of color parameters from said selected data members to express said given geometric position into an element of a color image, and
  c) a setup for repeating a) and b) for all geometric positions on said main path so that overall said trace is expressed into an image segment representing entire said main path within said target,
 whereby information arising from a plurality of repeated sound trips caused by repeated sound reflections by the exterior and interior interfaces of said target is complementarily incorporated into said color image such that the image is substantially more discriminative, descriptive, and position-sensitive to distributional acoustic characteristics of said target.

8. The ultrasonic apparatus of claim 7, wherein said array of sequenced numerical data is selected from a group comprising: (a) digitized trace without substantial modification, (b) Fourier transforms of said digitized trace, (c) inverse convolutions or de-convolutions using said digitized trace as a source function, (d) impulse responses otherwise derived from said digitized trace, (e) digital data after digital signal processing for suppressing background noises, (f) digital data after digital signal processing for emphasizing contributions of pre-selected physical effects imposed by said target, (g) digital data after digital signal processing for separating contributions among said repeated sound trips, and any combinations of (a) through (g).

9. The ultrasonic apparatus of claim 7, further comprising: a setup for combining image segments of multiple said traces respectively representative of different main paths across said target in the sequential order of trace taking operation or in operator specified manner, regardless of relative geometric positioning among said main paths, to form a cross-sectional profile of said target, whereby the formed cross-sectional profile serves the purpose of comparing obtained image segments to identify abnormal interior condition, rather than generating rigorous image in traditional imaging sense.

10. The ultrasonic apparatus of claim 9, further comprising:
 a setup for storing a predetermined number of said multiple traces,
 devices such as a movable cursor allowing operator to select any image segment based on one of said stored traces,
 a setup for displaying additional information based on said stored trace independently of the display of said cross-sectional profile, wherein said additional information is selected from a group comprising:
 entire or a selected portion of said trace, entire or a selected portion of transformed or modified said trace, entire or a selected portion of an impulse response based on said trace, thickness reading and other numeric quantifies characterizing said trace, numeric quantities characterizing multiple stored traces as a group, and any combinations thereof,
 whereby the apparatus performs the functionality of ultrasonic thickness gauging, ultrasonic flaw detection, and other ultrasonic inspection tasks using said cross-sectional profile as a visual organizing and accessing tool.

* * * * *